United States Patent
Nakashima et al.

(10) Patent No.: US 10,625,098 B2
(45) Date of Patent: Apr. 21, 2020

(54) PARTICLE IRRADIATION SYSTEM AND PARTICLE THERAPY SYSTEM

(71) Applicant: Hitachi, Ltd., Tokyo (JP)

(72) Inventors: Yuto Nakashima, Tokyo (JP); Takamichi Aoki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/392,663

(22) Filed: Apr. 24, 2019

(65) Prior Publication Data

US 2019/0329070 A1  Oct. 31, 2019

(30) Foreign Application Priority Data

Apr. 26, 2018 (JP) ................................ 2018-085006

(51) Int. Cl.
| | |
|---|---|
| *A61N 5/10* | (2006.01) |
| *H05H 7/04* | (2006.01) |
| *H05H 13/04* | (2006.01) |
| *H05H 9/00* | (2006.01) |

(52) U.S. Cl.
CPC ......... *A61N 5/1043* (2013.01); *A61N 5/1078* (2013.01); *H05H 7/04* (2013.01); *A61N 2005/1087* (2013.01); *H05H 9/00* (2013.01); *H05H 13/04* (2013.01); *H05H 2007/046* (2013.01)

(58) Field of Classification Search
USPC .......................... 250/492.3, 396 R, 396 ML
See application file for complete search history.

(56) References Cited

U.S. PATENT DOCUMENTS

2013/0001432 A1* 1/2013 Jongen ..................... A61N 5/10
250/396 R
2017/0229281 A1 8/2017 Furukawa et al.

FOREIGN PATENT DOCUMENTS

JP      2016-83344 A   5/2016

* cited by examiner

*Primary Examiner* — Kiet T Nguyen
(74) *Attorney, Agent, or Firm* — Mattingly & Malur, PC

(57) ABSTRACT

A particle irradiation system includes three or more scanning magnets that scan a beam in a vertical direction (first direction) or a horizontal direction (second direction) perpendicular to each other. The three or more scanning magnets are configured such that the scanning magnets and the scanning magnets for scanning in the same direction between the vertical direction or the horizontal direction, are disposed in series on a progressing direction axis of a beam, and a volume of a magnetic field feeding region decreases as the scanning magnet is installed at a position farther from an isocenter on the progressing direction axis.

7 Claims, 13 Drawing Sheets

PARTICLE IRRADIATION SYSTEM AND PARTICLE THERAPY SYSTEM

CROSS-REFERENCE TO RELATED APPLICATION

The present application claims priority from Japanese application JP 2018-085006, filed on Apr. 26, 2018, the contents of which is hereby incorporated by reference into this application.

BACKGROUND OF THE INVENTION

1. Field of the Invention

The present invention relates to a particle irradiation system and a particle therapy system. In particular, the present invention relates to a particle irradiation system and a particle therapy system that irradiate a target with a charged particle beam.

2. Description of the Related Art

As an example of charged particle beam irradiation system capable of suppressing an increase in size and securing a sufficient radiation field, JP 2016-83344 A discloses a charged particle beam irradiation system that includes a first scanning magnet device configured to bend a charged particle beam to a second direction that is substantially perpendicular to a first direction along which the charged particle beam enters; and a second scanning magnet device configured to bend the charged particle beam to a third direction that is substantially perpendicular to the first direction and the second direction, the first scanning magnet device and the second scanning magnet device being disposed to be parallel with the first direction.

SUMMARY OF THE INVENTION

In particle therapy, which is one of cancer treatment methods, a target volume is irradiated with charged particle beams such as protons and carbon ions.

In particle therapy systems used for such particle therapy, energy and spatial spread of the charged particle beam are adjusted to form a dose distribution conformal to a tumor shape.

The particle therapy system includes an accelerator, a beam transport system, and an irradiation system.

The accelerator is a system that accelerates a charged particle beam to energy to be used for treatment, and a synchrotron, a cyclotron, a synchro cyclotron, or the like can be exemplified as the accelerator used for the particle therapy.

The beam transport system transports the particle beam to a target position called an isocenter in a therapy room while adjusting a size of the particle beam using a quadrupole magnet or the like installed in the system.

The irradiation system is a system that forms the transported beam into a dose distribution conformal to a target tumor shape.

Examples of a method of forming the dose distribution include a scatterer irradiation method of causing a beam to hit against a scatterer to form a shape of the beam to a tumor shape and a scanning irradiation method of scanning a finely narrowed beam conformal to the tumor shape using a magnet called a scanning magnet.

In the scanning irradiation method of the latter, a target can be irradiated over a wider radiation field, as the radiation field, which is a scannable range on the target, increases.

In order to widen the radiation field with the scanning irradiation method, there are methods such as moving an installation position of the scanning magnet away from an isocenter, extending a pole length of the scanning magnet, and increasing an intensity of a magnetic field generated by the scanning magnet.

However, moving the installation position away from the isocenter or extending the pole length leads to an increase in size of the entire particle therapy system and a building including the particle therapy system, and thus, it is difficult to adopt such a method.

Here, the scanning magnet is generally provided with one dipole magnet for scanning in a certain direction and one dipole magnet for scanning in a direction perpendicular thereto. In JP 2016-83344 A, a sufficient radiation field is secured while suppressing an increase in size by installing such a pair of dipole magnets in parallel.

Further, scan velocity of a beam on a target is also important in the scanning irradiation method. The scan velocity depends on a time change rate of the intensity of the magnetic field generated by the scanning magnet, and the time change rate of the intensity of the magnetic field is determined by a time change rate of an excitation current.

Here, the time change rate of the excitation current is affected by an inductance of a coil. Thus, the scan velocity is improved by reducing the inductance.

Although reduction of the inductance of the scanning magnet is effective for the improvement of scan velocity in this manner, it is necessary to reduce the number of coil turns or to reduce a magnetic field feeding volume of a magnet for the reduction. However, the reduction of the number of coil turns leads to reduction of the radiation field due to reduction of a magnetomotive force.

Therefore, the pole length, and a pole width and an inter-pole gap need to be reduced for the reduction of the magnetic field feeding volume, but lead to the reduction of the radiation field and reduction of a region where the beam can pass in the scanning magnet, respectively, and thus, it is necessary to cope with the reduction of the magnetic field feeding volume using a new configuration.

An object of the present invention is to provide a particle irradiation system and a particle therapy system which have a wide radiation field, a high scan velocity, and a compact size.

The present invention includes a plurality of means for solving the above problems. According to an example thereof, a particle irradiation system includes three or more scanning magnets that scan a beam in a first direction or a second direction, which are perpendicular to each other. The three or more scanning magnets are configured such that at least two or more scanning magnets for scanning in an identical direction between the first direction and the second direction are disposed in series on a progressing direction axis of the beam, and that a volume of a magnetic field feeding region decreases as the scanning magnet is installed at a position farther from an isocenter on the progressing direction axis.

According to another example, a particle irradiation system includes three or more scanning magnets that scan a beam in a first direction or a second direction, which are perpendicular to each other. Among the three or more scanning magnets, at least two or more scanning magnets for scanning in an identical direction between the first direction and the second direction are disposed in series on a progressing direction axis of the beam, and a cross-sectional area of a magnetic field feeding region in a plane vertical to the progressing direction axis decreases as a distance from an isocenter increases on the progressing direction axis.

According to the present invention, it is possible to provide the particle irradiation system and the particle therapy system which have the wide radiation field, the high scan velocity, and the compact size. Other objects, configurations, and effects which have not been described above become apparent from embodiments to be described hereinafter.

DESCRIPTION OF THE PREFERRED EMBODIMENTS

Hereinafter, embodiments of a particle irradiation system and a particle therapy system of the present invention will be described using the drawings.

Although there is no particular statement regarding a particle beam irradiation method in each of embodiments to be described hereinafter, for example, the present invention is applied to a scanning irradiation system which uses an accelerator to generate a high-energy nuclear beam for use in particle therapy, transports the generated beam to the particle irradiation system, and scans the beam to a predetermined position in the particle irradiation system.

The scanning irradiation system is a system that arranges a fine dose distribution called a spot at each irradiation point in a target to form the dose distribution conformal to a shape of the target. Broadly speaking, there are a discrete spot scanning method and a raster scanning method.

The discrete spot scanning method is a method of stopping beam extraction while moving an irradiation point of a particle beam from one spot to the next spot and resuming the beam extraction after completion of the movement. The raster scanning method is a method of continuously performing irradiation without interruption of beam extraction while scanning the same slice.

First Embodiment

A particle irradiation system according to a first embodiment of the present invention will be described with reference to FIGS. 1 to 10.

Figure 1:
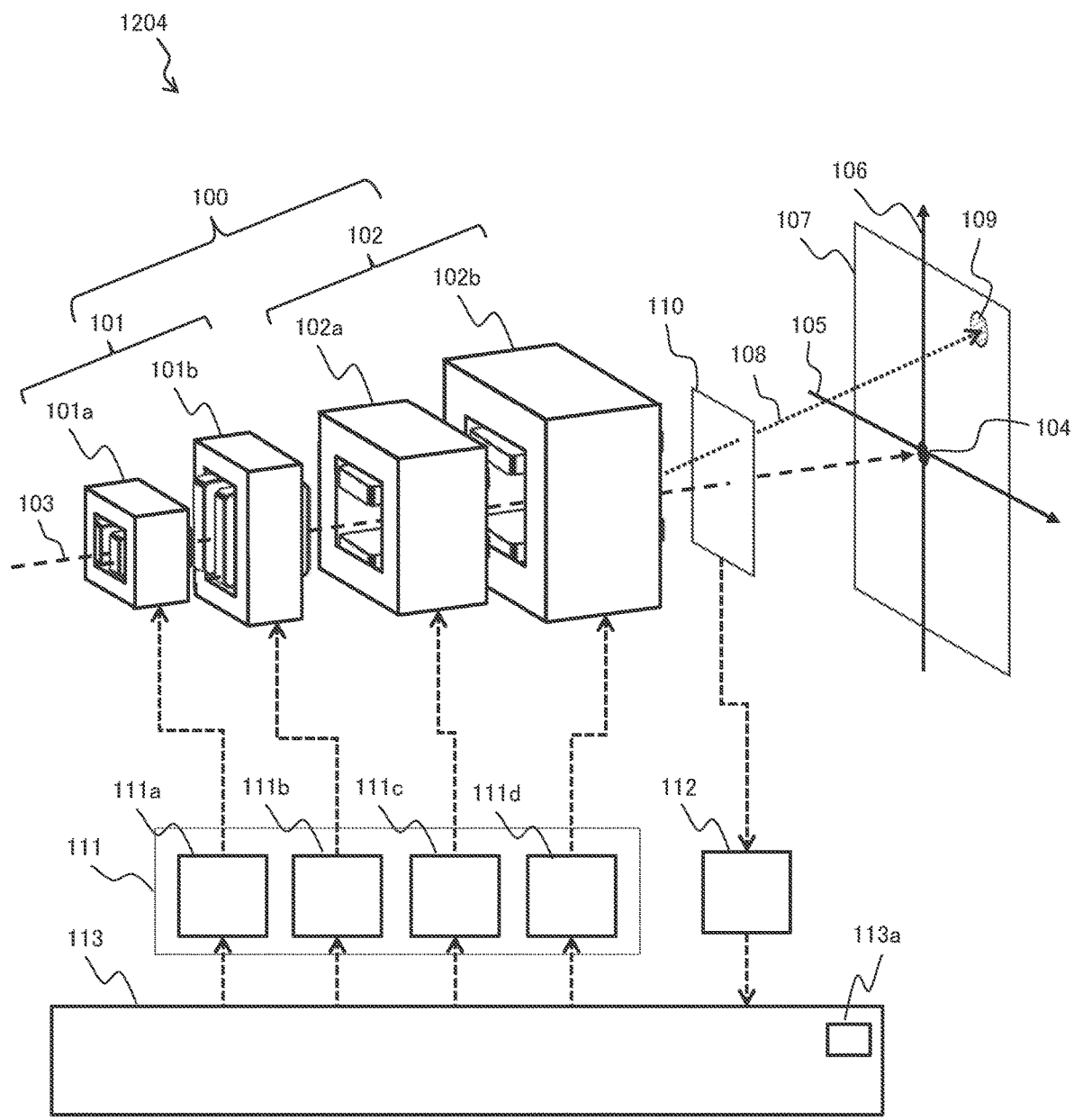
FIG. 1 is an entire configuration view of a particle irradiation system according to a first embodiment of the present invention.

First, a configuration of a particle irradiation system 1204 will be described with reference to FIG. 1. FIG. 1 illustrates an outline of the particle irradiation system of the present embodiment.

In FIG. 1, the particle irradiation system 1204 of the present embodiment includes, for example, a scanning magnet unit 100 installed along a progressing direction axis 103 of a beam, a beam position monitor 110, a power supply 111, a beam position monitor signal processor 112, and an irradiation system controller 113.

In the particle irradiation system 1204, a particle beam incident on the scanning magnet unit 100 progresses straight along the beam progressing direction axis 103 to reach an isocenter 104 at the time of non-scanning. In the present embodiment, two axes having the isocenter 104 as the origin and perpendicular to each other are defined as a horizontal axis 105 and a vertical axis 106.

The scanning magnet unit 100 includes a vertical axis direction scanning magnet unit 101 that scans a particle beam in a direction of the vertical axis 106 and a horizontal axis direction scanning magnet unit 102 that scans a particle beam in a direction of the horizontal axis 105.

The vertical axis direction scanning magnet unit 101 is constituted by two pairs of magnets of a first vertical scanning magnet 101a and a second vertical scanning magnet 101b.

Similarly, the horizontal axis direction scanning magnet unit 102 is also constituted by two pairs of magnets of a first horizontal scanning magnet 102a and a second horizontal scanning magnet 102b.

Power supplies 111a, 111b, 111c, and 111d are connected to the respective scanning magnets 101a, 101b, 102a, and 102b on a one-to-one basis in order to independently control each excitation amount of the first vertical scanning magnet 101a, the second vertical scanning magnet 101b, the first horizontal scanning magnet 102a, and the second horizontal scanning magnet 102b.

As a current is independently supplied from the scanning magnet power supplies 111a, 111b, 111c, and 111d to the vertical axis direction scanning magnet unit 101 and the horizontal axis direction scanning magnet unit 102, an orbit of a particle beam is bent along a scanning orbit 108, and an arbitrary beam irradiation point 109 on a radiation field 107 including the isocenter 104 is irradiated with the particle beam.

The beam position monitor signal processor 112 integrates electric signals detected by the beam position monitor 110 to calculate a passage position of the particle beam, and outputs a result of the calculation to the irradiation system controller 113.

The irradiation system controller 113 controls the beam irradiation point 109 by controlling the current supplied from the scanning magnet power supply 111 based on the calculation result of the beam position in the beam position monitor signal processor 112. The irradiation system controller 113 is constituted by one or more processors, a CPU, and the like, and control of an operation of each device is executed by various programs. This program is stored in a storage unit 113a, and read and executed by the CPU.

Figure 2:
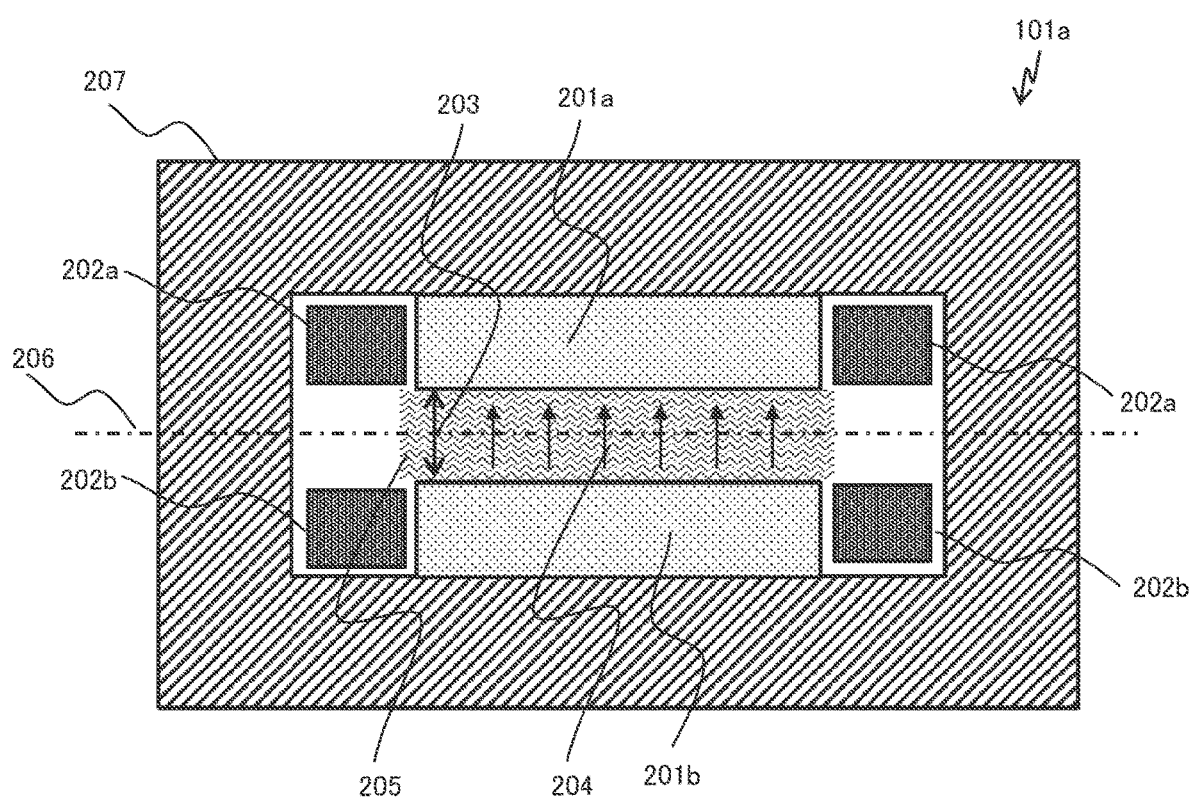
FIG. 2 is a cross-sectional view of a plane perpendicular to a beam progressing direction axis of a scanning magnet in the particle irradiation system of the first embodiment of the present invention.

Next, structures of the first vertical scanning magnet 101a and the second vertical scanning magnet 101b, the first horizontal scanning magnet 102a, and the second horizontal scanning magnet 102b in the particle irradiation system of the present embodiment will be described using the first vertical scanning magnet 101a as a representative. FIG. 2 is a cross-sectional view of a plane perpendicular to the progressing direction axis 103 of the first vertical scanning magnet 101a in the particle irradiation system of the present embodiment.

Incidentally, only a length of each pole (a pole width 302) and a length between poles 201a and 201b (an inter-pole gap 203) are different in the structures of the second vertical scanning magnet 101b, the first horizontal scanning magnet 102a, and the second horizontal scanning magnet 102b, and the main structures thereof are the same as the structure of the first vertical scanning magnet 101a, and thus, detailed descriptions thereof will be omitted.

The first vertical scanning magnet 101a is constituted by the poles 201a and 201b, coils 202a and 202b, and a yoke 207.

The pole 201a and the pole 201b oppose each other with a central plane 206 interposed therebetween, and are disposed at positions separated so as to secure a certain inter-pole gap 203.

In the first vertical scanning magnet 101a, a magnetic field 204 having an orientation substantially perpendicular to the central plane 206 is generated in the inter-pole gap 203 by the coil 202a and the coil 202b.

A particle beam that has passed through a magnetic field feeding region 205, which is a generation range of the above magnetic field 204, is bent in a direction substantially parallel to the central plane 206.

Figure 3:
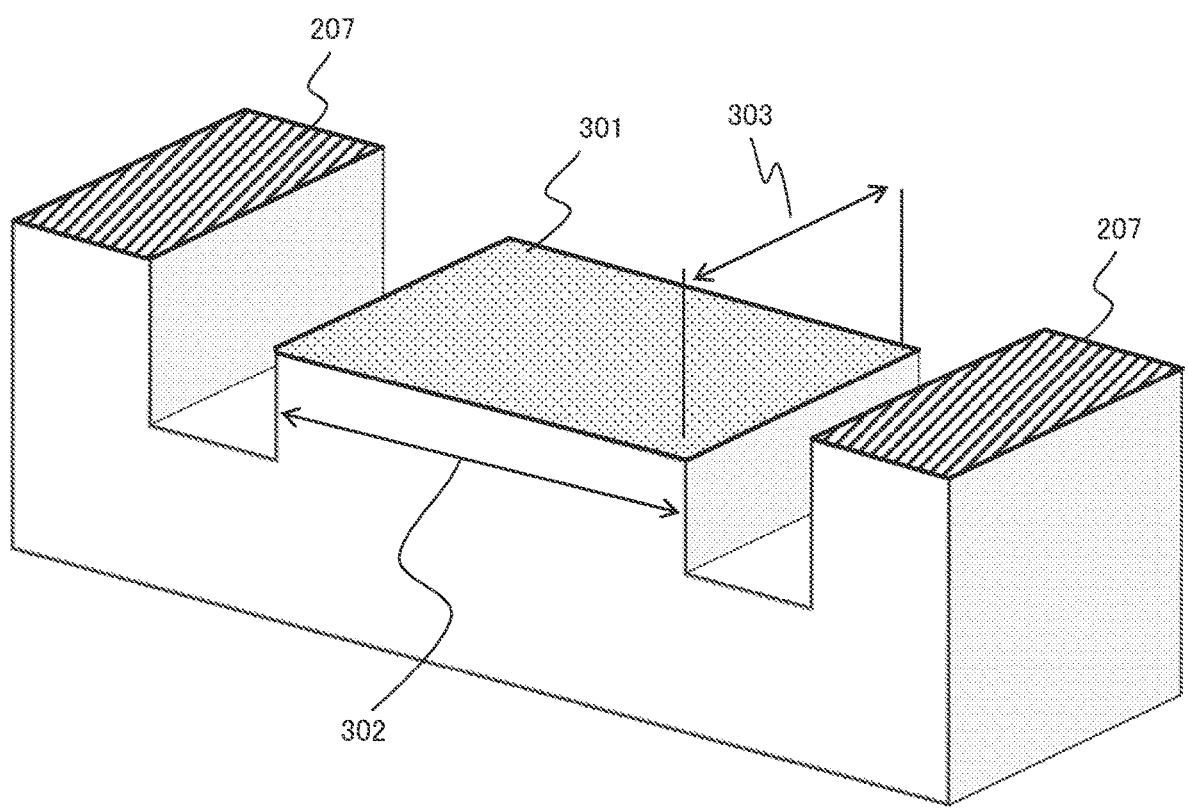
FIG. 3 is a perspective view of cross sections of a central plane of a scanning magnet pole and a yoke in the particle irradiation system of the first embodiment of the present invention.

FIG. 3 is a perspective view of the pole 201a, the pole 201b, and the yoke 207 of FIG. 2 cut along the central plane 206.

The magnetic field feeding region 205 is present so as to be interposed between two pole faces 301 which are faces of the pole 201a and the pole 201b substantially parallel to the central plane 206 during energization with respect to the coils 202a and 202b.

As illustrated in FIG. 2, the volume of the magnetic field feeding region 205 is roughly determined by a product of the inter-pole gap 203, the pole width 302, and a pole length 303.

Figure 4:
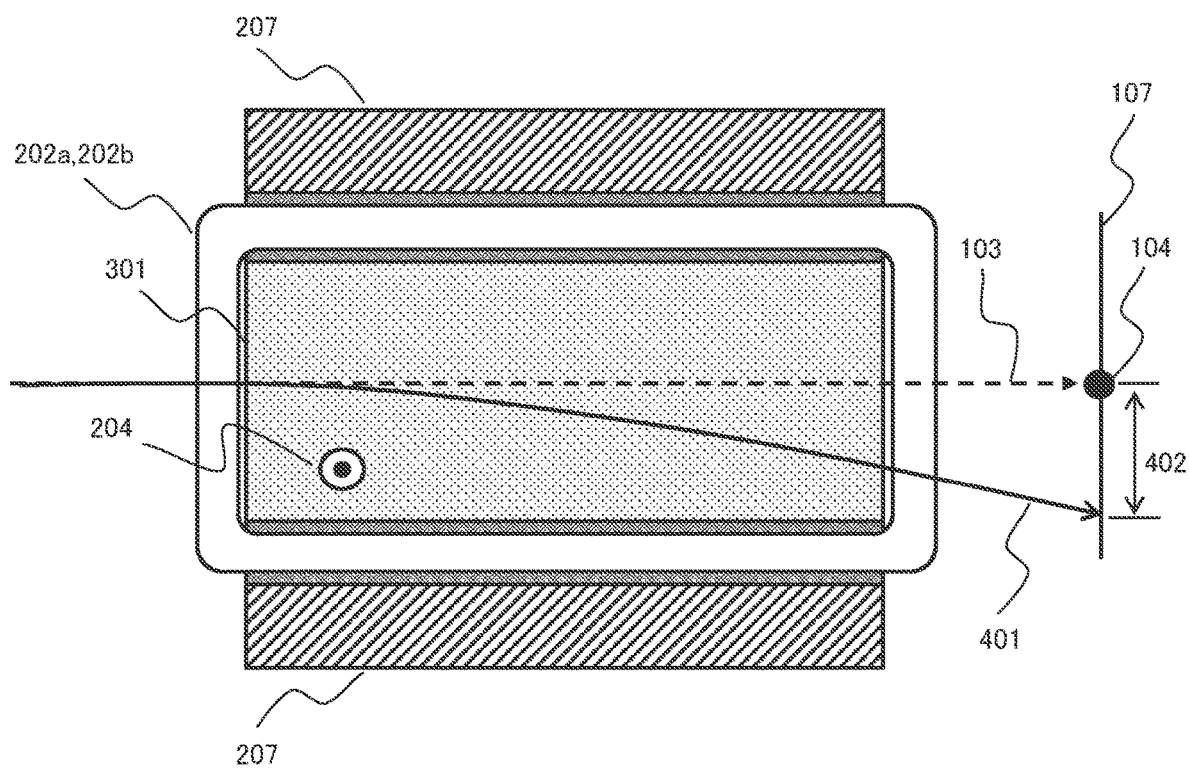
FIG. 4 is a cross-sectional view of a central plane of the scanning magnet in the particle irradiation system of the first embodiment of the present invention.
Figure 5:
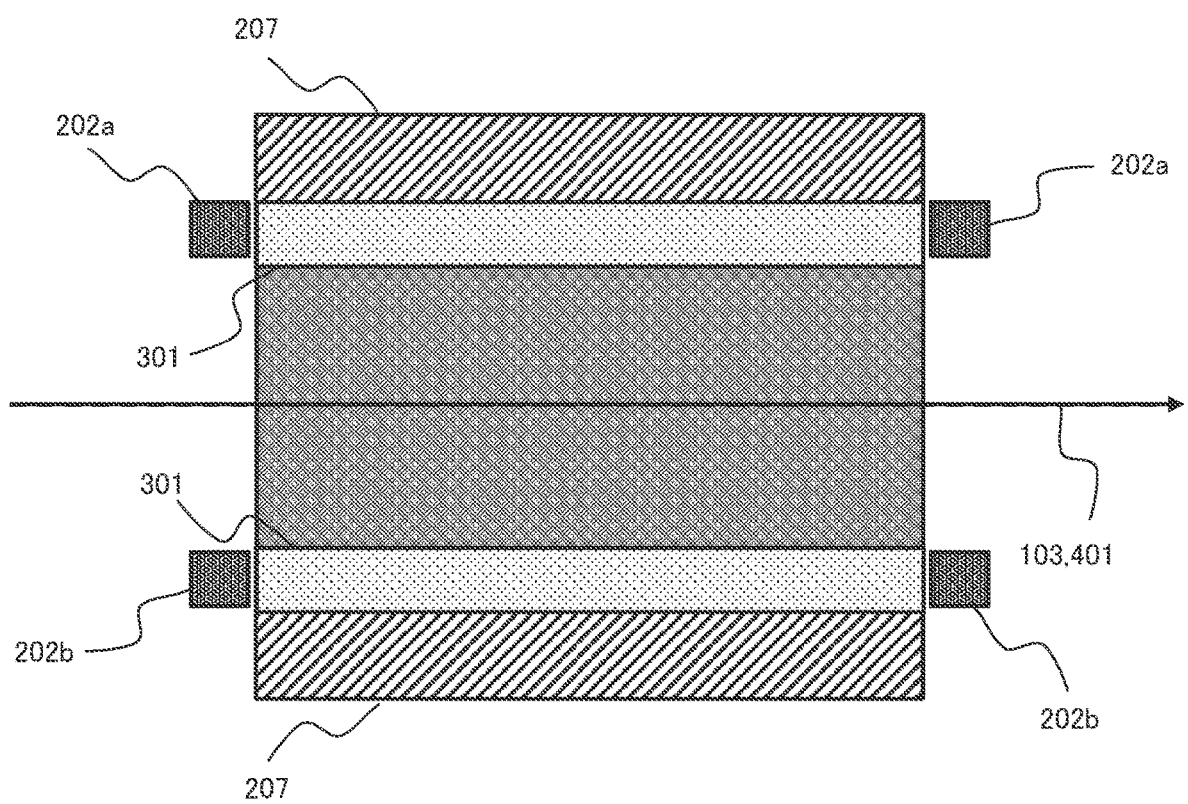
FIG. 5 is a cross-sectional view of a plane perpendicular to a central plane including the beam progressing direction axis of the scanning magnet in the particle irradiation system of the first embodiment of the present invention.

FIG. 4 is a cross-sectional view of the first vertical scanning magnet 101a of FIG. 2 along the central plane, and FIG. 5 is a cross-sectional view of the first vertical scanning magnet 101a of FIG. 2 along a plane that includes the beam progressing direction axis and is perpendicular to the central plane.

As illustrated in FIG. 2, the magnetic field 204 is generated in a direction perpendicular to the paper surface by supplying the current to the coils 202a and 202b in the first vertical scanning magnet 101a.

Hereinafter, a description will be given regarding a case where a certain beam position on the radiation field 107 is irradiated with a particle beam along a scanning orbit 401 as illustrated in FIGS. 4 and 5 by causing a DC current to flow through the coil 202a of the first vertical scanning magnet 101a.

Assuming that a distance (scanning distance 402) between the beam position and the isocenter 104 as illustrated in FIG. 4 is D and the magnitude of the DC current is I in this case, D and I have a substantially proportional relationship.

Next, a change rate of the scanning distance when the scanning distance 402 changes from zero to D, that is, scan velocity will be described. At this time, the DC current changes from zero to I. Assuming that the change rate of the current is dI/dt, scan velocity $v_{scan}$ can be obtained as in the following Formula (1).

[Formula 1]

$$v_{scan} = \frac{D}{I}\frac{dI}{dt} \qquad (1)$$

In general, the change rate of the current is slower than the desired scan velocity due to the presence of inductances of the coils 202a and 202b. Therefore, the necessary scan velocity is obtained by feeding a voltage called a forcing voltage to the coils 202a and 202b.

Here, if assuming that an inductance of a circuit including the coils 202a and 202b is L and the forcing voltage fed to the circuit from the power supply is $V_{force}$, the change rate dI/dt of the current can be obtained as the following Formula (2).

[Formula 2]

$$\frac{dI}{dt} = \frac{V_{force}}{L} \qquad (2)$$

As a result, by substituting Formula (2) for Formula (1), the scan velocity $v_{scan}$ can be obtained as the following Formula (3).

[Formula 3]

$$v_{scan} = \frac{DV_{force}}{LI} \qquad (3)$$

As illustrated in Formula (3), the scan velocity can be improved by reducing the inductance L.

It is known that the inductance L has a relationship of Formula (4) with magnetic energy W in the scanning magnet and the coil current I.

[Formula 4]

$$L = \frac{2W}{I^2} \quad (4)$$

Further, it is known that the magnetic energy W can be obtained by Formula (5).

[Formula 5]

$$W = \tfrac{1}{2}\int_V H \cdot B \, d^3 x \quad (5)$$

In Formula (5), H indicates a magnetic field, B indicates a magnetic flux density, and an integration range is a volume V of the magnetic field feeding region.

It is understood that the magnetic energy W generally decreases as the volume V of the magnetic field feeding region decreases as illustrated in Formula (5), and the inductance L also decreases as the magnetic energy W decreases, that is, the volume V of the magnetic field feeding region decreases as illustrated in Formula (4).

Here, as described above, the volume of the magnetic field feeding region 205 of the first vertical scanning magnet 101a, the second vertical scanning magnet 101b, the first horizontal scanning magnet 102a, or the second horizontal scanning magnet 102b is determined by the product of the inter-pole gap 203, the pole width 302, and the pole length 303.

Further, the inter-pole gap 203 and the pole width 302 are determined by the maximum scanning distance, that is, a beam passage region at the time of scanning the beam to an end of the radiation field 107. Further, the maximum scanning distance is determined by a value (BL product) obtained by integrating the magnetic field 204 in a range determined by the pole length 303 on the beam progressing direction axis 103.

That is, even when the configuration of the scanning magnet is different, the magnitude of the maximum scanning distance does not change as long as a sum of BL products of magnets through which beams pass is constant.

Therefore, when two scanning magnets, obtained by halving only a pole length from a certain scanning magnet, are installed in series, an inductance per scanning magnet can be substantially halved, and the maximum scanning distance can be made to be substantially the same as the maximum scanning distance of the original scanning magnet.

Figure 6:
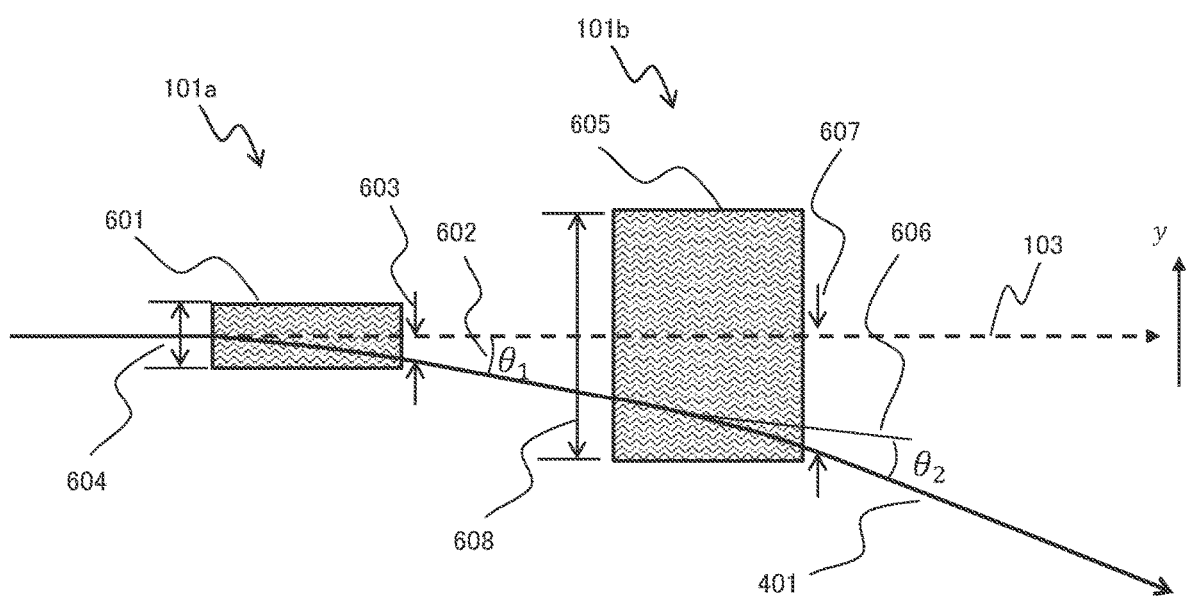
FIG. 6 is a schematic view of a magnetic field feeding region of a vertical axis direction scanning magnet unit and a beam orbit at the time of beam scanning in the vertical axis direction in the particle irradiation system of the first embodiment of the present invention.

FIG. 6 is a schematic view of beam scanning using the vertical axis direction scanning magnet unit 101 in the particle irradiation system of the present embodiment.

In the present embodiment, magnetic field feeding regions of the vertical axis direction scanning magnet unit 101 and the horizontal axis direction scanning magnet unit 102 exist at four places, in total, in series on the progressing direction axis 103.

When two magnetic field feeding regions including one by the first vertical scanning magnet 101a and one by the second vertical scanning magnet 101b exist in the vertical axis direction scanning magnet unit 101 as in the present embodiment, a first magnetic field feeding region 601 and a second magnetic field feeding region 605 are formed respectively from the upstream side of the progressing direction axis 103 as viewed from the isocenter 104 as illustrated in FIG. 6.

As a current is independently supplied to each of the two scanning magnets 101a and 101b for excitation in the vertical axis direction scanning magnet unit 101, magnetic fields are applied to the first magnetic field feeding region 601 and the second magnetic field feeding region 605.

The BL product in the vertical axis direction scanning magnet unit 101 is represented by a sum of BL products of the first magnetic field feeding region 601 and the second magnetic field feeding region 605. A value of the current supplied to each scanning magnet can be arbitrarily set since the power supplies 111a and 111b are independently configured. For example, the current value is adjusted such that the sum of BL products becomes the highest within a range where the current can be supplied from each of the scanning magnet power supplies 111a and 111b when bending the beam at the maximum scanning distance.

The particle beam that has passed through the first magnetic field feeding region 601 and the second magnetic field feeding region 605 is bent by a first bending angle 602 and a second bending angle 606, respectively as illustrated in FIG. 6.

When the end of the radiation field 107 is irradiated with the beam, the beam passes positions separated from the progressing direction axis by a first maximum beam passage width 603 and a second maximum beam passage width 607, respectively, at exits of the first magnetic field feeding region 601 and the second magnetic field feeding region 605.

Here, the maximum beam passage width becomes narrower toward the upstream side of the progressing direction axis 103 as illustrated in FIG. 6, and a first magnetic field feeding width 604 can be set to smaller than a second magnetic field feeding width 608. Thus, it is possible to make the inter-pole gap 203 of the first vertical scanning magnet 101a forming the first magnetic field feeding region 601 narrower than the inter-pole gap 203 of the second vertical scanning magnet 101b forming the second magnetic field feeding region 605.

In the present embodiment, the sizes of the inter-pole gap 203 and the pole width 302 are kept constant without being changed in the individual scanning magnets 101a, 101b, 102a, and 102b as illustrated in FIGS. 6 to 9.

Figure 7:
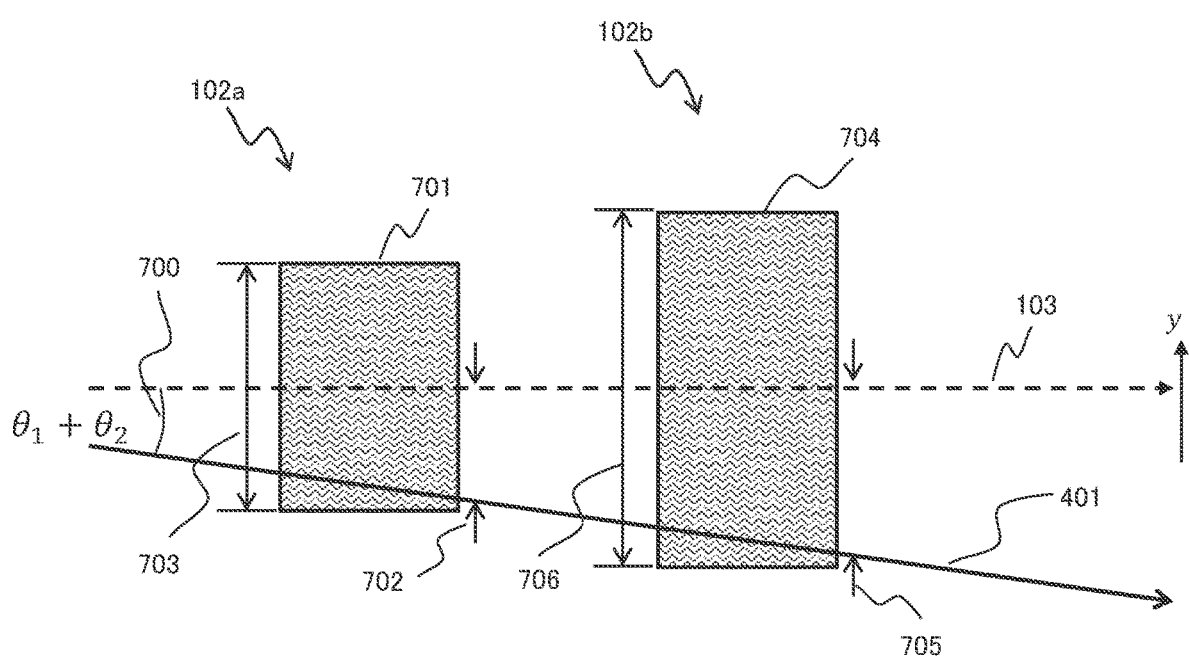
FIG. 7 is a schematic view of a magnetic field feeding region of a horizontal axis direction scanning magnet unit and the beam orbit at the time of beam scanning in the vertical axis direction in the particle irradiation system of the first embodiment of the present invention.

FIG. 7 is a schematic view of the magnetic field feeding region of the horizontal axis direction scanning magnet unit 102 and the beam orbit at the time of scanning a beam only in the vertical axis direction in the particle irradiation system of the present embodiment.

Hereinafter, a description will be given regarding a case where a particle beam bent in the vertical axis direction by the vertical axis direction scanning magnet unit 101, installed in series on the upstream side of the progressing direction axis 103, is bent by the horizontal axis direction scanning magnet unit 102.

When the end of the radiation field 107 is irradiated with a beam as illustrated in FIG. 7, the beam is bent by a sum 700 of the first bending angle 602 and the second bending angle 606 by the vertical axis direction scanning magnet unit 101 and enters the horizontal axis direction scanning magnet unit 102 as described above.

Thus, the beam passes positions separated from the progressing direction axis by a first maximum beam passage width 702 and a second maximum beam passage width 705, respectively, at exits of a first magnetic field feeding region 701 and a second magnetic field feeding region 704.

Therefore, even for the horizontal axis direction scanning magnet unit 102, it is possible to make a first magnetic field feeding width 703 in the horizontal axis direction of the first magnetic field feeding region 701, formed by the first horizontal scanning magnet 102a positioned on the upstream side, smaller than a second magnetic field feeding width 706 in the horizontal axis direction of the second magnetic field feeding region 704 formed by the second horizontal scanning magnet 102b.

Further, even in the vertical axis direction of the horizontal axis direction scanning magnet unit 102, it is possible to make the inter-pole gap 203 of the first horizontal scanning magnet 102a forming the first magnetic field feeding region 701 narrower than the inter-pole gap 203 of the second horizontal scanning magnet 102b forming the second magnetic field feeding region 704.

Figure 8:
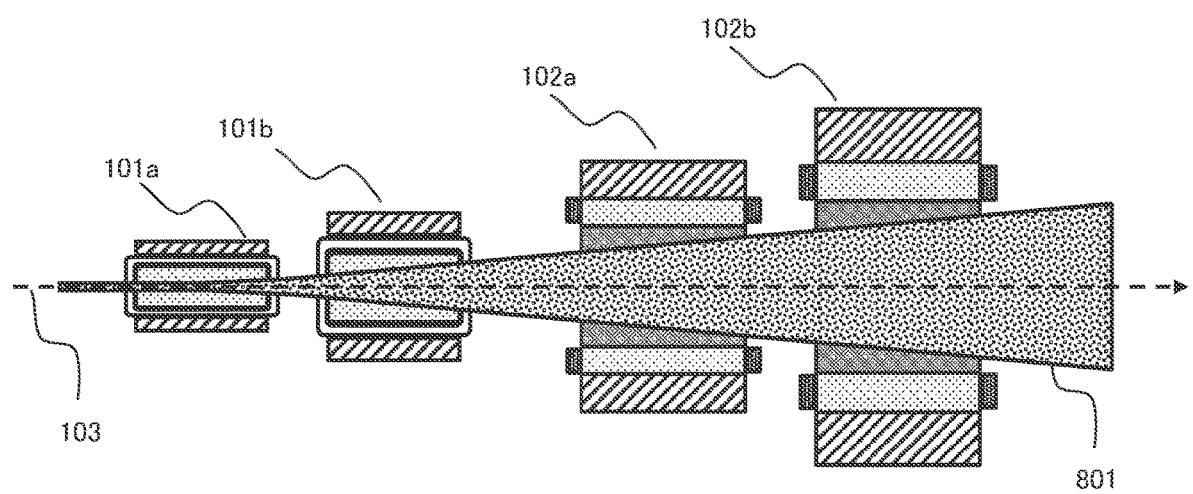
FIG. 8 is a cross-sectional view along a plane including a vertical axis of the scanning magnet unit and the beam progressing direction axis in the particle irradiation system of the first embodiment of the present invention.

FIG. 8 is a cross-sectional view along a plane including the vertical axis 106 of the scanning magnet unit 100 and the progressing direction axis 103 in the particle irradiation system 1204 of the present embodiment.

As illustrated in FIG. 8, sizes of the respective inter-pole gaps 203 and the respective pole widths 302 are designed such that the respective magnetic field feeding regions formed by the first vertical scanning magnet 101a, the second vertical scanning magnet 101b, the first horizontal scanning magnet 102a, and the second horizontal scanning magnet 102b in the scanning magnet unit 100 include a vertical axis direction maximum beam passage region 801 spreading toward the downstream side of the progressing direction axis 103.

At this time, the vertical axis direction scanning magnet unit 101 is installed on the upstream side of the progressing direction axis 103 as compared with the horizontal axis direction scanning magnet unit 102, and thus, not only the pole widths 302 of the first vertical scanning magnet 101a and the second vertical scanning magnet 101b but also the inter-pole gaps 203 of the first horizontal scanning magnet 102a and the second horizontal scanning magnet 102b become narrower on the upstream side than on the downstream side.

It is possible to improve the magnetic field intensity even under the same magnetomotive force by shortening the inter-pole gap 203, and thus, a sum of BL products can be set to be equal to or greater than that of a single scanning magnet having the same sum of pole lengths.

Figure 9:
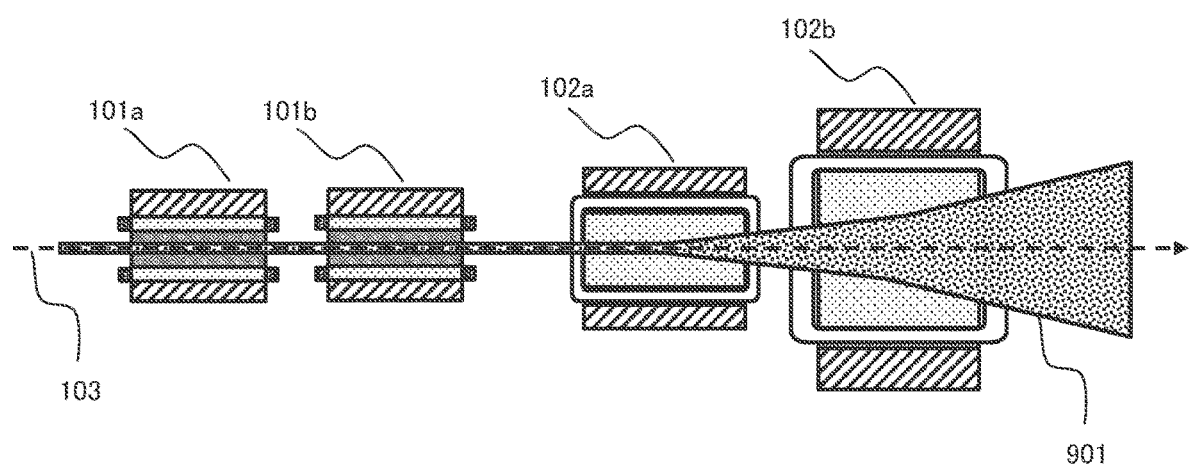
FIG. 9 is cross-a sectional view along a plane including a horizontal axis of the scanning magnet unit and the beam progressing direction axis in the particle irradiation system of the first embodiment of the present invention.

FIG. 9 is a cross-sectional view along a plane including the horizontal axis 105 of the scanning magnet unit 100 and the progressing direction axis 103 in the particle irradiation system 1204 of the present embodiment.

Even regarding the magnetic field feeding region in the horizontal axis direction, sizes of the respective inter-pole gaps and the respective pole widths of the first vertical scanning magnet 101a, the second vertical scanning magnet 101b, the first horizontal scanning magnet 102a, and the second horizontal scanning magnet 102b are designed so as to include a horizontal axis direction maximum beam passage region 901 as illustrated in FIG. 9.

Therefore, the pole width 302 is narrower in the first horizontal scanning magnet 102a on the upstream side than in the second horizontal scanning magnet 102b on the downstream side.

Further, a width of the horizontal axis direction maximum beam passage region 901 is constant before passing through the horizontal axis direction scanning magnet unit 102, and thus, both the inter-pole gaps 203 in the horizontal axis direction of the first vertical scanning magnet 101a and the second vertical scanning magnet 101b have the same width as illustrated in FIG. 9.

Here, when considering the volume of each magnetic field feeding region based on the widths of the magnetic field feeding regions in the vertical axis direction and horizontal axis direction of each of the scanning magnets 101a, 101b, 102a, and 102b, the volume of the magnetic field feeding region at the position away from the isocenter 104 on the progressing direction axis 103, that is, on the upstream side is smaller than the volume of the magnetic field feeding region on the downstream side.

That is, when two scanning magnets are used for the vertical axis direction scanning magnet unit 101 and the horizontal axis direction scanning magnet unit 102, respectively, and designed such that the volume of each magnetic field feeding region is smaller on the upstream side than on the downstream side, it is possible to design the scanning magnets to include the entire beam passage region.

Figure 10:
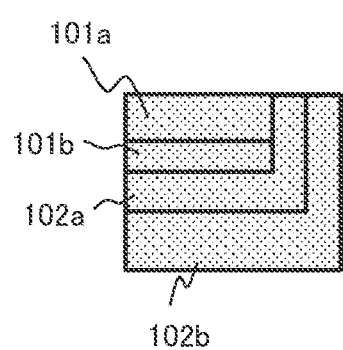
FIG. 10 is a view comparing cross-sectional areas of magnetic field feeding regions of the scanning magnet in the particle irradiation system of the first embodiment of the present invention.

In such a case, a cross-sectional area of the magnetic field feeding region 205 along the plane vertical to the progressing direction axis 103 decreases as a distance from the isocenter 104 increases on the progressing direction axis 103 as illustrated in FIG. 10.

Next, effects of the present embodiment will be described.

The particle irradiation system 1204 according to the first embodiment of the present invention described above includes the three or more scanning magnets 101a, 101b, 102a, and 102b that scan the beam in the vertical direction or the horizontal direction, which are perpendicular to each other. The three or more scanning magnets 101a, 101b, 102a, and 102b are configured such that at least two or more of the scanning magnets 101a and 101b and the scanning magnets 102a and 102b for scanning in the same direction between the vertical direction and the horizontal direction, are disposed in series on the beam progressing direction axis 103, and the volume of the magnetic field feeding region 205 is smaller as the scanning magnet 101a, 101b, 102a, or 102b is installed at the position farther from the isocenter 104 on the progressing direction axis 103. Further, the cross-sectional area of the magnetic field feeding region 205 along the plane vertical to the progressing direction axis 103 decreases as the distance from the isocenter 104 increases on the progressing direction axis 103.

Accordingly, the pole width 302 and the inter-pole gap 203 of the magnet gradually spreads in accordance with the beam passage regions, for example, as compared with the case of being installed as JP 2016-83344 A described above, and thus, the space occupied by a coil or a pole for scanning in the other direction inside the yoke 207 is eliminated. In particular, the pole width 302 and the inter-pole gap 203 can be narrowed by the scanning magnet on the upstream side. Therefore, it is possible to increase the BL product and reduce an inductance per scanning magnet, and it is possible to achieve expansion of the radiation field and an increase of the scan velocity accompanying an increase of the magnetic field intensity. Further, a length in the beam progressing direction can be shortened by the increase of the BL product, and it is possible to achieve miniaturization of the particle irradiation system 1204.

Further, the three or more scanning magnets 101a, 101b, 102a, and 102b are configured such that the sizes of the inter-pole gap 203 and the pole width 302 are constant among the individual scanning magnets 101a, 101b, 102a, and 102b, and thus, the scanning magnets are easily manufactured, and it is possible to reduce cost of the particle irradiation system 1204.

Since the power supplies 111a, 111b, 111c, and 111d, which independently control each excitation amount of the three or more scanning magnets 101a, 101b, 102a, and 102b and are connected to the scanning magnets 101a, 101b, 102a, and 102b on a one-to-one basis, are further provided, the current in accordance with the specification of each scanning magnet and each required scanning amount can be supplied to each scanning magnet, and it is possible to improve the degree of freedom in control. Further, it is possible to more easily achieve the increase of the scan velocity, and the irradiation accuracy can be secured.

Although the case of installing the horizontal axis direction scanning magnet unit 102 on the downstream side of the vertical axis direction scanning magnet unit 101 has been described, the horizontal axis direction scanning magnet unit can be installed on the upstream side of the vertical axis direction scanning magnet unit.

That is, the order of installation from the upstream side to the downstream side in the progressing direction of the first horizontal scanning magnet 102a, the second horizontal scanning magnet 102b, the first vertical scanning magnet 101a, and the second vertical scanning magnet 101b is arbitrarily set in accordance with required size of a radiation field and scan velocity. However, scanning magnets for scanning in the same direction need to be installed continuously such that a scanning magnet for scanning in a different direction is not interposed therebetween.

Further, the number of installed scanning magnets for scanning in the horizontal axis direction and the number of installed scanning magnets for scanning in the vertical axis direction may be one or more, and may be three or more in total.

For example, only one of the horizontal axis direction scanning magnet or the vertical axis direction scanning magnet may be provided, and two or more of the other may be provided. In this case, it is possible to achieve an effect that the inter-pole gap is further narrowed, and thus, it is desirable to provide one scanning magnet of either the horizontal axis direction or the vertical axis direction on a side installed on the downstream side, and to provide two or more scanning magnets of the other on a side installed on the upstream side.

Although the case where each of the scanning magnets includes only one pair of the coils 202a and 202b as the coils generating the magnetic field for bending has been described in the present embodiment, a plurality of pairs of coils may be provided in each magnet.

Further, the current supplied from the scanning magnet power supplies 111a, 111b, 111c, and 111d may be applied in series or in parallel from the same power supply with respect to the scanning magnets for scanning in the same direction. For example, the power supply for the first vertical scanning magnet 101a and the power supply for the second vertical scanning magnet 101b can be shared, and the power supply for the first horizontal scanning magnet 102a and the power supply for the second horizontal scanning magnet 102b can be shared. Incidentally, it is desirable not to share the power supply for the scanning magnets in different directions.

Second Embodiment

A particle irradiation system according to a second embodiment of the present invention will be described with reference to FIGS. 11 and 12. The same configurations as those in the first embodiment are denoted by the same reference signs, and descriptions thereof will be omitted. The following embodiments will be also described in the same manner.

Figure 11:
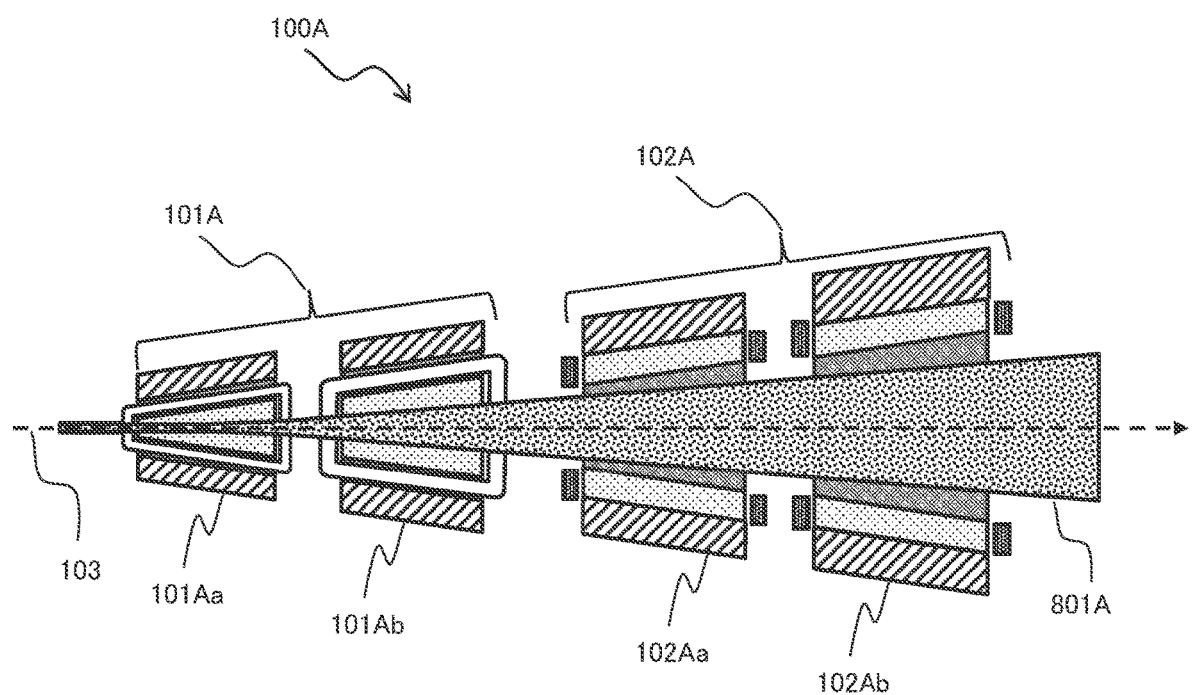
FIG. 11 is a cross-sectional view along a plane including a vertical axis of a scanning magnet unit and a beam progressing direction axis in a particle irradiation system of a second embodiment of the present invention.

FIG. 11 is a cross-sectional view along a plane including a vertical axis of a scanning magnet unit and a beam progressing direction axis in the present embodiment. FIG. 12 is a cross-sectional view along a plane including a horizontal axis of the scanning magnet unit and the beam progressing direction axis in the present embodiment.

The particle irradiation system of the present embodiment is basically constituted by the same elements as the particle irradiation system 1204 of the first embodiment illustrated in FIG. 1. A difference is that a scanning magnet unit 100A is provided instead of the scanning magnet unit 100.

Figure 12:
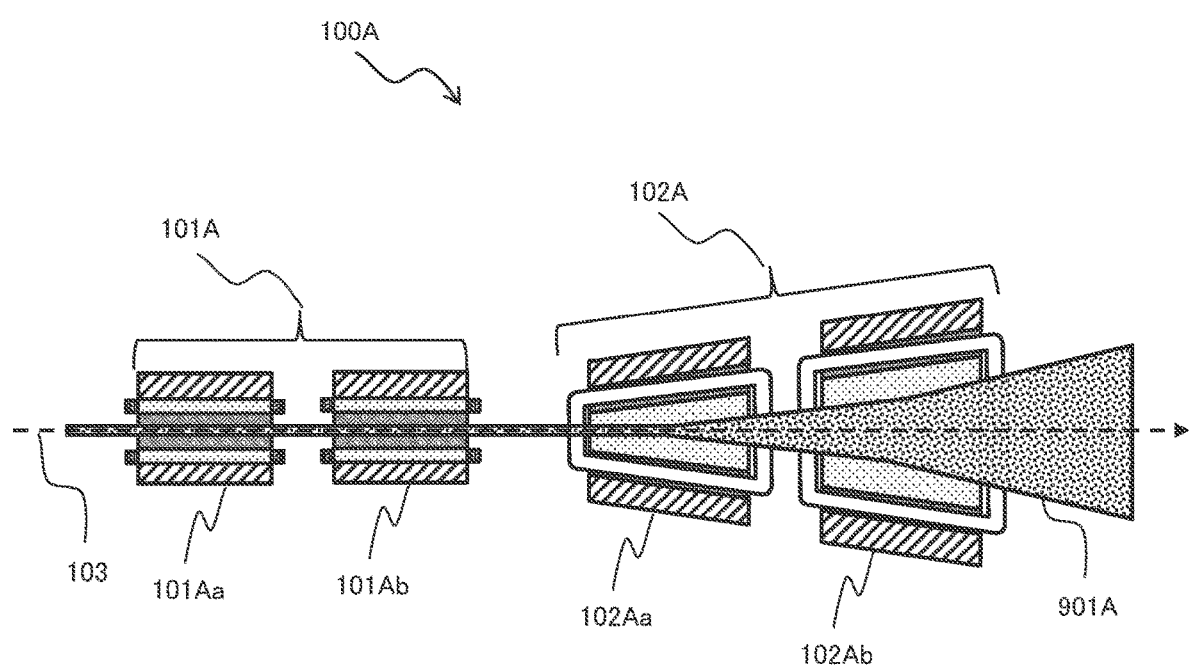
FIG. 12 is cross-a sectional view along a plane including a horizontal axis of the scanning magnet unit and the beam progressing direction axis in the particle irradiation system of the second embodiment of the present invention.

As illustrated in FIGS. 11 and 12, the scanning magnet unit 100A of the present embodiment includes a vertical axis direction scanning magnet unit 101A and a horizontal axis direction scanning magnet unit 102A, which is similar to the scanning magnet unit 100 of the first embodiment.

The vertical axis direction scanning magnet unit 101A is constituted by a first vertical scanning magnet 101Aa and a second vertical scanning magnet 101Ab. The horizontal axis direction scanning magnet unit 102A is constituted by a first horizontal scanning magnet 102Aa and a second horizontal scanning magnet 102Ab.

As illustrated in FIG. 11, the first vertical scanning magnet 101Aa, the second vertical scanning magnet 101Ab, the first horizontal scanning magnet 102Aa, and the second horizontal scanning magnet 102Ab are configured such that the yoke 207, the pole width 302, and the inter-pole gap 203 in each scanning magnet have shapes spreading linearly toward the downstream side of the progressing direction axis 103 conformal to a vertical axis direction maximum beam passage region 801A and a horizontal axis direction maximum beam passage region 901A.

In other words, the sizes of the inter-pole gap 203 and the pole width 302 are designed to be narrowed as the distance from the isocenter 104 increases on the progressing direction axis 103.

Since a width of the horizontal axis direction maximum beam passage region 901A is constant before passing through the horizontal axis direction scanning magnet unit 102A, the inter-pole gaps 203 in the horizontal axis direction of the first vertical scanning magnet 101Aa and the second vertical scanning magnet 101Ab have the same width as illustrated in FIG. 12.

The other configurations and operations are substantially the same as the configurations and operations of the particle irradiation system of the first embodiment described above, and details thereof will be omitted.

Substantially the same effects as those of the particle irradiation system of the first embodiment described above can be also obtained in the particle irradiation system of the second embodiment of the present invention.

Further, at least two or more of the scanning magnets are configured such that the sizes of the inter-pole gap 203 and the pole width 302 decrease as the distance from the isocenter 104 increases on the progressing direction axis 103 in each scanning magnet, and thus, can make a shape of a magnetic field feeding region closer to a shape of the beam passage region. Therefore, it is possible to more effectively increase a BL product and reduce an inductance per scanning magnet, and it is possible to more effectively achieve expansion of a radiation field and an increase of scan velocity.

Further, sizes of the inter-pole gap 203 and the pole width 302 are constant in some of the individual scanning magnets so that the shape of the beam passage region in the direction scanned by the scanning magnet on the downstream side does not change in the scanning magnet on the upstream side, and thus, it is possible to make the shape of the magnetic field feeding region of the scanning magnet on the upstream side conformal to the shape of the beam passage region.

Although the yoke, the pole width, and the inter-pole gap spread linearly in the present embodiment, the shape can be formed as a curved shape or a stepped shape as long as the shape includes the vertical axis direction maximum beam passage region 801 and the horizontal axis direction maximum beam passage region 901.

Further, a shape of the yoke on an outer peripheral side is not limited to the case of spreading toward the downstream side of the progressing direction axis 103, but can be formed as a shape parallel to the progressing direction axis 103.

Further, the scanning magnet disposed in the particle irradiation system of the first embodiment described above can be used as some of the scanning magnets of the present embodiment.

Third Embodiment

A particle therapy system according to a third embodiment of the present invention will be described with reference to FIG. 13.

Figure 13:
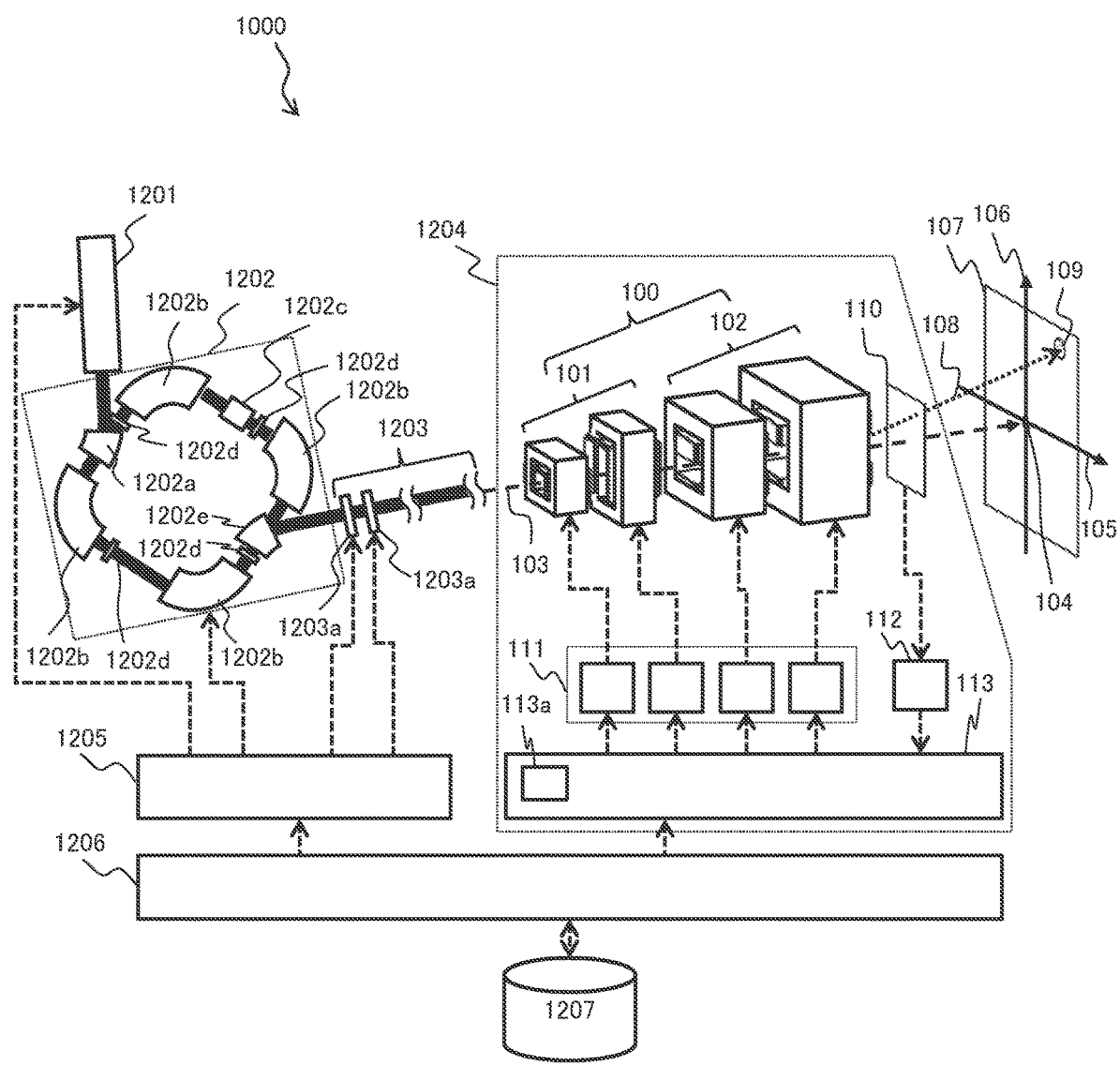
FIG. 13 is an overall configuration diagram of a particle therapy system according to a third embodiment of the present invention.

FIG. 13 is an entire configuration diagram of a particle therapy system according to the third embodiment of the present invention.

As illustrated in FIG. 13, a particle therapy system 1000 of the present embodiment includes a linac 1201, a synchrotron 1202, a beam transport system 1203, the particle irradiation system 1204 described in the first embodiment, an accelerator beam transport system controller 1205, a particle therapy system controller 1206, and a database 1207.

The particle irradiation system described in the second embodiment can be used instead of the particle irradiation system 1204 described in the first embodiment.

The linac 1201 and an injector 1202*a* are connected to the synchrotron 1202, and ions before being accelerated, which have been generated by the linac 1201, are incident from the injector 1202*a*.

The incident ions are finely adjusted by a magnetic field generated by a quadrupole magnet 1202*d* or the like and circulated in a substantially square path formed by four bending magnets 1202*b*, and are accelerated whenever passing through an accelerating cavity 1202*c*. A beam accelerated to predetermined energy is introduced into the beam transport system 1203 from an extraction port 1202*e*.

The beam transport system 1203 includes a plurality of quadrupole magnets 1203*a* and bending magnets (not illustrated), and is connected to the synchrotron 1202 and the particle irradiation system 1204. A particle beam extracted from the synchrotron 1202 is converged by the quadrupole magnets 1203*a* while passing through the beam transport system 1203, and is changed in direction by the bending magnets to be incident on the particle irradiation system 1204.

A part of the beam transport system 1203 and the particle irradiation system 1204 are installed in a substantially cylindrical gantry in a therapy room and can be configured to rotate with the gantry, but can be also configured to be fixed.

The particle therapy system controller 1206 sends a command to the accelerator beam transport system controller 1205 and the irradiation system controller 113 based on irradiation data (treatment planning) created based on information such as a depth and a shape of a target volume stored in the database 1207.

The accelerator beam transport system controller 1205 controls devices constituting the linac 1201 and the synchrotron 1202 to accelerate the particle beam to energy suitable for therapy. Further, the accelerator beam transport system controller 1205 controls devices constituting the beam transport system 1203 to transport the particle beam accelerated to the predetermined energy to the particle irradiation system 1204.

The particle therapy system controller 1206 controls the scanning magnet power supply 111 through the irradiation system controller 113 to perform beam irradiation control suitable for treatment in the radiation field 107.

The particle therapy system controller 1206, the accelerator beam transport system controller 1205, and the irradiation system controller 113 are constituted by one or a plurality of processors, a CPU, and the like Control of an operation of each device is executed by various programs. This program is stored in an internal recording medium such as the database 1207 and the storage unit 113*a*, and is read and executed by the CPU.

A control process of operations to be executed may be grouped into one program or may be divided into a plurality of programs, or a combination thereof may be adopted. Some or all of the programs may be realized by dedicated hardware or may be modularized. Further, various programs may be installed in each computer by a program distribution server or an external storage medium.

The respective controllers may be independent systems connected via a wired or wireless network, or two or more controllers may be integrated.

The configurations and operations of the particle irradiation system are the same as those of the particle irradiation system according to the first embodiment or the second embodiment described above, and details thereof will be omitted.

According to the particle therapy system of the third embodiment of the present invention, it is possible to realize both an increase of scan velocity or the like and miniaturization by providing the particle irradiation system of the first embodiment or the particle irradiation system of the second embodiment described above.

Although the case of adopting the linac 1201 and the synchrotron 1202 as the accelerator has been described in the present embodiment, other types of accelerators, such as a cyclotron and a synchrocyclotron, can also be adopted.

Although the therapy system including one accelerator and one irradiation system has been described, a particle therapy system can be configured to include a plurality of irradiation systems for one accelerator, and the particle irradiation system 1204 of the first embodiment or the particle irradiation system of the second embodiment can be appropriately provided in each irradiation system.

Although the case of using the beam transport system 1203 has been described, a particle beam can be transported directly from the accelerator to the particle irradiation system.

Further, a heavy particle beam such as a carbon beam and a helium beam or a proton beam can be used as the particle beam used for therapy.

OTHERS

Incidentally, the present invention is not limited to the above-described embodiments, and includes various modification examples. The above-described embodiments have been described in detail in order to describe the present invention in an easily understandable manner, and are not necessarily limited to one including the entire configuration that has been described above.

Further, configurations of another embodiment can be also substituted for some configurations of a certain embodiment, and further, a configuration of another embodiment can be added to a configuration of a certain embodiment. Further, addition, deletion or substitution of other configurations can be also made with respect to some configurations of each embodiment.

What is claimed is:

1. A particle irradiation system, comprising:
three or more scanning magnets that scan a beam in a first direction or a second direction, which are perpendicular to each other,
wherein the three or more scanning magnets include a first scanning magnet, a second scanning magnet, a third scanning magnet and a fourth scanning magnet, which are disposed in a series along a progression direction of an axis of the beam toward an isocenter such that the second scanning magnet is disposed after the first scanning magnet, the third scanning magnet is disposed after the second scanning magnet and the fourth scanning magnet is disposed after the third scanning magnet,
wherein the first scanning magnet and the second scanning magnet scan the beam in the first direction,
wherein the third scanning magnet and the fourth scanning magnet scan the beam in the second direction, and
wherein respective volumes of respective magnetic field feeding regions of the of the first scanning magnet, second scanning magnet, third scanning magnet and fourth scanning magnet increase in series from the first scanning magnet to the fourth scanning magnet.

2. The particle irradiation system according to claim 1, wherein respective sizes of an inter-pole gap and a pole width are constant in each of the scanning magnets.

3. The particle irradiation system according to claim 1, wherein among two of the three or more scanning magnets, a size of an inter-pole gap and a pole width of one of the scanning magnets that is closest to the isocenter is greater than a size of an inter-pole gap and a pole width of the other of the two scanning magnets.

4. The particle irradiation system according to claim 3, wherein some of the three or more scanning magnets is configured such that the sizes of the inter-pole gap and the pole width are constant in each of the scanning magnets.

5. The particle irradiation system according to claim 1, further comprising
power supplies that independently control each excitation amount of the three or more scanning magnets and are connected to the scanning magnets on a one-to-one basis.

6. A particle therapy system comprising the particle irradiation system according to claim 1.

7. A particle irradiation system, comprising:
three or more scanning magnets that scan a beam in a first direction or a second direction, which are perpendicular to each other,
wherein the three or more scanning magnets include a first scanning magnet, a second scanning magnet, a third scanning magnet and a fourth scanning magnet, which are disposed in a series along a progression direction of an axis of the beam toward an isocenter such that the second scanning magnet is disposed after the first scanning magnet, the third scanning magnet is disposed after the second scanning magnet and the fourth scanning magnet is disposed after the third scanning magnet,
wherein the first scanning magnet and the second scanning magnet scan the beam in the first direction,
wherein the third scanning magnet and the fourth scanning magnet scan the beam in the second direction, and
wherein respective cross-sectional areas of magnetic field feeding regions in a plane vertical to the progressing direction axis of the of the first scanning magnet, second scanning magnet, third scanning magnet and fourth scanning magnet increase in series from the first scanning magnet to the fourth scanning magnet.

* * * * *